United States Patent [19]
McKenna et al.

[11] Patent Number: 5,948,931
[45] Date of Patent: Sep. 7, 1999

[54] PREPARATION AND USE OF α-(HYDROXYIMINO) PHOSPHONOACETIC ACIDS

[75] Inventors: Charles E. McKenna, Pacific Palisades; Boris A. Kashemirov, Venice, both of Calif.

[73] Assignee: University of Southern California, Los Angeles, Calif.

[21] Appl. No.: 08/893,656

[22] Filed: Jul. 11, 1997

Related U.S. Application Data

[60] Provisional application No. 60/022,527, Jul. 12, 1996.
[51] Int. Cl.[6] .......................................................... C07F 9/40
[52] U.S. Cl. ............................ 558/172; 560/168; 562/17
[58] Field of Search ........................... 558/172; 560/168; 562/17

[56] References Cited

PUBLICATIONS

CA:67:32306, abs of Zh Obsch Kihim, by Nifant'ev ,37(2), pp. 511–512, 1967.
CA:125:137094 abs of Bioctal Biotransform, by Rakels, 13 (3) pp. 179–188, 1996.
CA: 123:12200 correction of 121:108990 by McKenna, J Chem Soc Chem Commun, 10, pp. 1211–1212, 1994.
CA:121:108990 in J Chem Soc Chem Commun by McKenna 10 pp. 1211–1212, 1994.

*Primary Examiner*—Gary Geist
*Assistant Examiner*—Jean F Vollano
*Attorney, Agent, or Firm*—Fulbright & Jaworski

[57] ABSTRACT

α-(hydroxyimino)phosphonoacetic acids (also referred to as "α,α-disubstituted trifunctional oximes" and "Troika Acids") and their derivatives, and methods to prepare them are disclosed. Also disclosed are the structures and fragmentation pathways of the α-(hydroxyimino)phosphonoacetic acids. The α-(hydroxyimino)phosphonoacetic acids and derivatives are useful as pH sensitive chelating agents, enzyme activated drugs, drug delivery agents, phosphorylating reagents and photo-activated reagents.

13 Claims, 6 Drawing Sheets

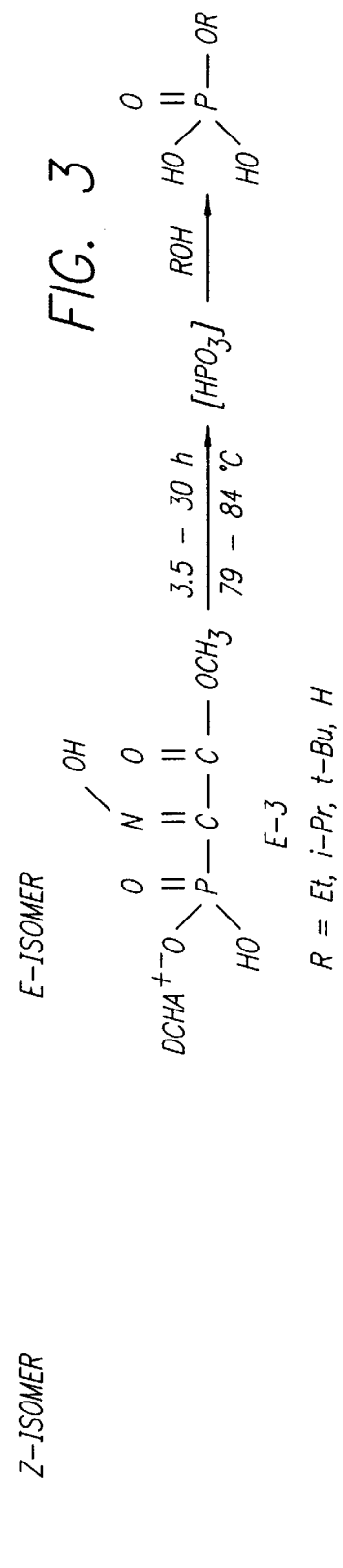
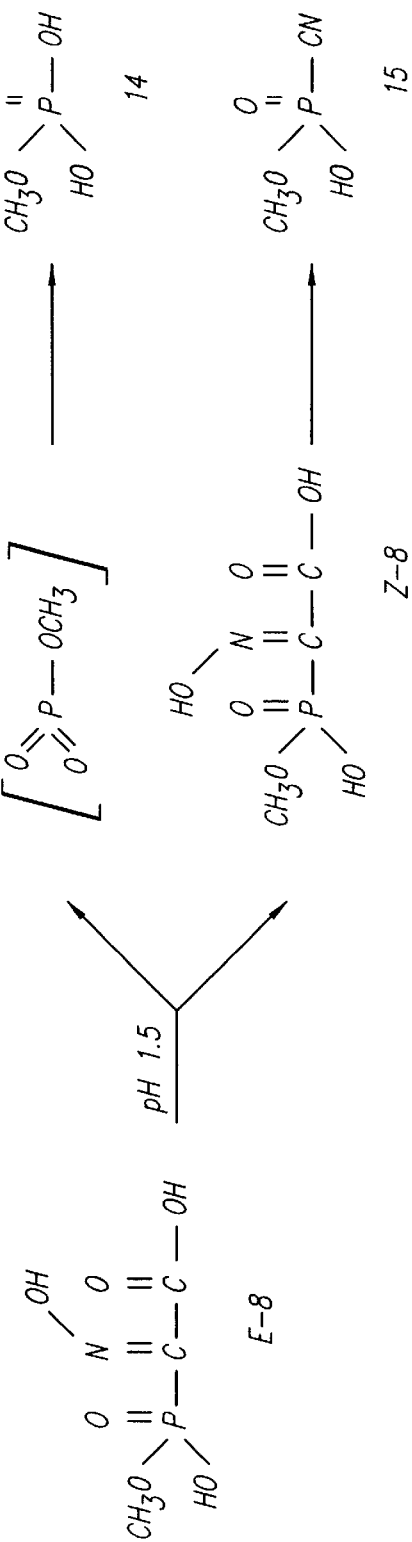

PREPARATION AND USE OF α-(HYDROXYIMINO) PHOSPHONOACETIC ACIDS

This application has priority to provisional application 60/022,527 filed Jul. 12, 1996.

FIELD OF INVENTION

This invention relates to the general field of phosphorus chemistry, and is particularly concerned with α-(hydroxyimino) phosphonoacetic acids, their derivatives, and methods for their synthesis.

BACKGROUND

Phosphonates play a significant role in the fields of chemistry, biology and medicine. They are endowed with special physical, chemical and biological properties which can make them uniquely useful. Various uses of phosphonate compounds include the design of novel metal chelators and biologically active compounds. For example, phosphonates have been used as inhibitors of enzymes which catalyze reactions of carboxylates or phosphates.

Due to their widespread applications, considerable activity has been devoted to developing convenient methods for synthesis of phosphonates or related compounds. Monomeric metaphosphate, for example, has been investigated as a highly reactive, electrophilic phosphorylation intermediate. Recently, investigations have emphasized the desirability of designing new precursors that can function as phosphorylating agents under physiological or other mild conditions.

For the foregoing reasons, there is a need to discover novel phosphonates or related compounds, and methods for synthesizing them in a simple, rapid, efficient manner with high yields. Further, it would be advantageous to have these compounds because they have widespread applications.

SUMMARY

The present invention is directed to α-(hydroxyimino) phosphonoacetic acids, their derivatives, and methods for their synthesis, that meets the above-mentioned needs. Regioselective monodealkylation with NaI or didealkylation with bromotrimethylsilane-ROH of esters of the α-(hydroxyimino)phosphonoacetic acids gives on treatment with a sufficient amount of dicyclohexylamine, followed by alkaline hydrolysis, high product yields of both the E- and Z-isomers of the α-(hydroxyimino)phosphonoacetic acids.

The method of the present invention can have wide applicability in selectively producing stereoisomers of α-(hydroxyimino)phosphonoacetic acids. Additionally, the method is short, simple, efficient and utilizes inexpensive starting materials. The present invention can also produce such stereoisomers at relatively low cost.

More particularly, the methods of the present invention convert phosphonates of the general formula:

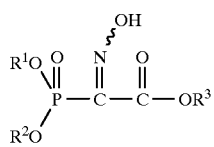

where $R^1$, $R^2$, and $R^3$ is hydrogen or when present as substituents may be any alkyl or aromatic group, selected from the group consisting of methyl, ethyl, propyl, butyl, benzyl, phenyl or a high group as desired.

Typically, the first step is treatment of the ester of the α-(hydroxyimino)phosphonoacetic acids with bromotrimethylsilane, followed by methanolysis to yield the C-ester of the α-(hydroxyimino)phosphonoacetic acids.

According to the present invention, two different workups can yield either E-α-(hydroxyimino)phosphonoacetic acid or Z-α-(hydroxyimino)phosphonoacetic acid.

Treatment of the C-ester of the α-(hydroxyimino) phosphonoacetic acid with a sufficient quantity of dicyclohexylamine, followed by recrystallization from methanol/ether forms the E- mono-dicyclohexylammonium salt.

Unexpectedly, slow evaporation of solvent to crystallize the C-ester of the α-(hydroxyimino)phosphonoacetic acid, followed by a sufficient quantity of dicyclohexylamine, and recrystallization from any method known to those skilled in the art, preferably from 1-propanol/acetone, forms pure Z-bis-dicyclohexylammonium salt.

Alkaline hydrolysis of the E-mono-dicyclohexylammonium and the Z-bis-dicyclohexylammonium salt yields the corresponding sodium salts.

Typically, heating of the E-mono-dicyclohexylammonium salt can be in any aqueous solvent known in the art. Preferably, the solvent is selected from the group consisting of ethanol-isopropanol, ethanol-t-butanol and water yields metaphosphate-like fragmentation phosphate products corresponding to the solvent the salt was heated in. For example, ethanol-isopropanol solvent can yield ethyl phosphate and isopropyl phosphate.

At pH values from about 6 to about 7, the E- and Z-sodium salts of α-(hydroxyimino)phosphonoacetic acid typically fragmented stereospecifically. Preferably, the E-sodium salt yields orthophosphoric acid. Also preferably, the Z-sodium salt yields phosphorocyanidic acid.

These and other features, aspects, and advantages of the present invention will become better understood with reference to the following description and appended claims.

BRIEF DESCRIPTION OF THE DRAWINGS

These and other features, aspects, and advantages of the present invention will become better understood with regard to the following description, appended claims, and accompanying drawings where:

FIG. 1 shows prototypic Troika acids;

FIG. 3 shows fragmentation of the E isomer with heat;

FIG. 5. shows pH fragmentation of (E)-(hydroxyimino)-(hydroxymethoxyphosphinyl)acetic acid;

DETAILED DESCRIPTION

Figure 2:
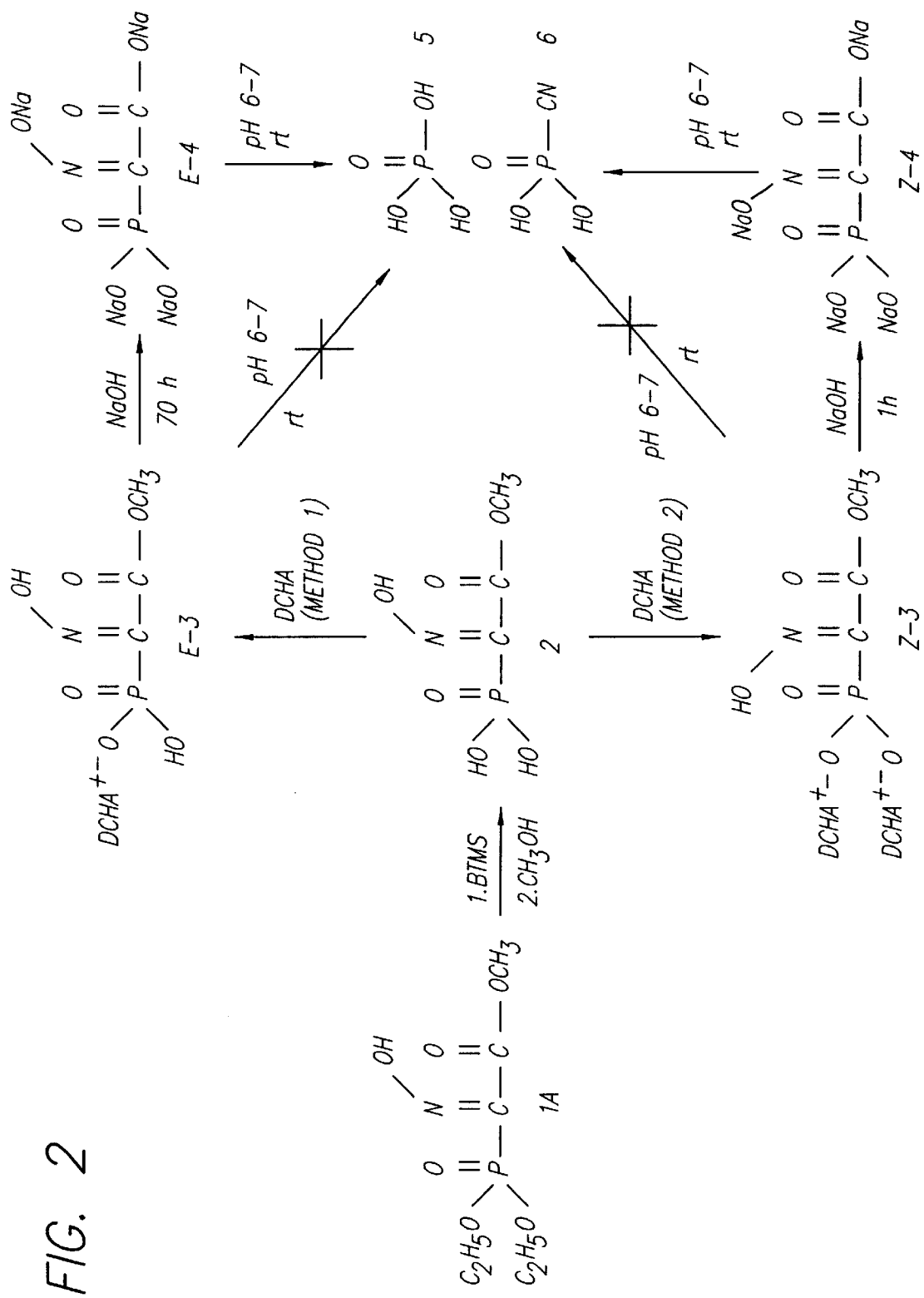
FIG. 2 shows the synthesis of Z and E isomers of the C-methyl Troika acid, and fragmentation pathways of the parent Troika acids.

According to one aspect of the present invention, there is provided α-(hydroxyimino) phosphonoacetic acids (herein also referred to as "α, α-disubstituted trifunctional oximes", "(hydroxyimino)(dihydroxyphosphinyl)acetic acids" and "Troika acids") their derivatives, and methods for their synthesis. Also disclosed are the structures and fragmentation pathways of the Troika acids. The present invention also includes the many uses of Troika acids and derivatives. For example, they can be used as either starting materials or end products in the making of the following useful materials: pH-sensitive chelating agents, enzyme activated drugs, drug delivery agents, phosphorylating reagents and photoactivated reagents.

The following references are incorporated herein by reference in their entirety, including cited references:

1. Kashemirov, B. A., et al., "'Troika Acids': Synthesis, Structure, and Fragmentation Pathways of Novel α-(Hydroxyimino)phosphonoacetic Acids", *J Am. Chem. Soc.*, 117:7285–7286 (1995); Supplemental Material, I. Synthetic Procedures and Spectroscopic Data, II. X-Ray Structural Data, III. Observed and Calculated Structure Factors for E-.Methyl α-(Hydroxyimino)-phosphonoacetate Mono-DCHA Salt and Z-Methyl α-(hydroxyimino) phosphonoacetate Bis-DCHA Salt.

2. Kashemirov, B. A., et al., "(E)-(Hydroxyimino)-(hydroxymethoxyphosphinyl)acetic Acid: Synthesis and pH-Dependent Fragmentation", *Tetra. Lett.*, 36:9437–9440 (1995).

3. McKenna, Charles E., et al., "(Hydroxyimino) phosphonoacetic Acids: Synthesis, Stereochemistry and Reactivity", *Phosphorus, Sulfur and Silicon*, 111:158 (1996).

4. Kashemirov, B. A., et al., "Synthesis of p-Nitrophenyl (E)-(Dihydroxyphosphinyl)(Hydroxyimino)Acetate—A New Agent for Phosphorylation Under Mild Aqueous Conditions", Abstract 248, ACS National Meeting(1996).

A chemical compound embodying features of the present invention can have the general formula:

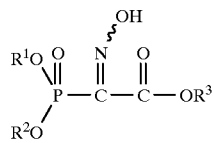

where $R^1$, $R^2$, and $R^3$ when present as substituents are each independently hydrogen, substituted or unsubstituted alkyl, alkenyl, alkynyl, or aryl.

The present invention is related to phosphonate, oxime and carboxylate moieties anchored to a common carbon atom: α-(hydroxyimino)phosphonoacetic acids—"Troika acids" (see FIG. 1). Due to the unique central location of the oxime hydroxy group, this group can interact via hydrogen-bonding with either of its two neighboring groups, depending on whether the group is in either E or Z orientation.

According to the present invention, the oxime hydroxy group can direct the course of reaction taken by a molecule under particular conditions. In addition, the α-carboxyl group can provide modulation of the hydroxyiminophosphonate moiety's activity as a phosphorylating reagent: chemical (or possibly enzymatic) unmasking of a neutral Troika acid carboxyl derivative such as a C-ester or C-amide to generate the free carboxylic acid (or carboxylate anion), can result in a substantially modified interaction with the oxime hydroxy (and possibly phosphonate) groups. Furthermore, such a C-group-dependent P-activation process can be mediated by a reagent or catalyst that is highly specific for the C-moiety.

C-alkyl and C-aryl esters of the parent compound "Troika acid" [α-(hydroxyimino)phosphonoacetic acid] are relatively stable at neutral pH or other mild conditions at room temperatures. Furthermore, the (E) and (Z) isomers of the esters and also their parent structures have distinct properties. Furthermore, the (E) isomers of the esters can be phosphorylating agents when heated in appropriate solvents.

Removal of the C-ester group from the (E) isomer of a C-ester-protected Troika acid generates the parent Troika acid, which can be an active phosphorylating agent in or near the physiological pH range, or below, at ambient temperature. Similar treatment of the distinct, corresponding (Z) isomer of a C-ester protected Troika acid results in formation of a previously uncharacterized compound, phosphorocyanidic acid [$(HO)_2P(O)CN$].

Troika acid species can be generated by specific reactions at a site on Troika acid derivatives remote from the phosphonate group, namely the carboxyl group, in the form of an ester, amide or other carboxyl derivative of the parent Troika structure. The specific reactions could include, but are not limited to: (a) modification of the ester moiety in C-ester-protected Troika acids to activate it to attack by nucleophiles or other specific reagents; (b) addition of metal ions, such as $Mg^{2+}$, $Ni^{2+}$ or others to Troika acid derivatives such as C-alkyl-protected Troika acids, which is found to cause similar activation dependent on the nature of the metal used; (c) modification of the ester moiety in the aforementioned C-ester Troika derivatives to make it susceptible to photochemical cleavage, by UV or visible light irradiation.

This principle can be extended to other methods of activation of a Troika acid precursor molecule or derivative, such as incorporation of a moiety X in the CO-X function of the Troika acid derivative (e.g., ester, peptide or other linkage) in which X also is, or includes a part, susceptible to specific recognition, binding, and hydrolysis (or other form of cleavage) by an enzyme, including catalytic antibodies raised for this purpose. A general method for preparing such Troika acid conjugates as described herein is disclosed in this invention. In addition, such cleavage could be achieved by appropriately lowering the pH of the reaction mixture.

A further use of this principle is attachment of the modified or unmodified Troika acid moiety via an ester, amido, or similar linker (with suitable spacer) to an insoluble polymeric support. The resulting novel immobilized Troika acid would have use in chelating specific metals, which if desired, could be released by one of the cleavage methods disclosed above, e.g., by adjustment of the pH. Such materials could be used to remove or recover valuable metals or undesirable metals as cations from sample solutions, such samples could include waste waters and sea water.

The materials and principle described in the present application could be used to deliver drugs for analytical purposes, such as used in Position Emission Tomography (PET) scanning or in other methods for delivery of radiopharmaceuticals to specific tissue sites, such as bone or targeted organs.

This invention could be used as a method for the indirect, condition- and/or reagent-specific generation of cyanide as well as for phosphorylations. For example, modification as suggested herein can be used to create a molecule specifically activated and cleaved by an enzyme activity characteristic of e.g., a malignant tumor cell resulting in release of metaphosphoric acid and cyanide which might thereby damage or kill the targeted cell with beneficial effect to the patient.

P-monoalkyl Troika acids can be prepared and have useful properties, e.g., as novel phosphorylating agents.

Similarly, modification can be carried out at the oxime group of Troika acid or its derivatives to create =N—OR ethers in which the R moiety can be designed for a purpose as outlined analogously in detail above for the C-ester derivatives.

Methods of Making α-α-Disubstituted Trifunctional Oximes

The methods of the present invention provide novel, uniquely effective procedures for rapidly, simply and inexpensively producing the two E and Z isomers of pure Troika acid.

One aspect according to the present invention, is the synthesis of both the E and Z isomers of the C-methyl Troika acid, (methyl α-(hydroxyimino)phosphonoacetic acid) 2 (see FIG. 2). The E-isomer of methyl α-(hydroxyimino) phosphonoacetic acid 2 is stable in any aqueous solvent known to those skilled in the art, but preferably $H_2O$ at physiological pH, but on aqueous alkaline cleavage of the carboxylate ester group typically, by those methods known to those skilled in the art, can generate the E-Troika acid, which proves to be an active phosphorylating agent at about pH 5–8, preferably about pH 6–7.

Methyl α-(hydroxyimino)phosphonoacetic acid 2, can be obtained on regioselective didealkylation by methods known to those in the art, of P, P-diethyl C-methyl ester 1A (E:Z, 4:1; $^{31}P$ NMR) preferably with 3 eq. $Me_3SiBr$ (BTMS) in refluxing $CH_2Cl_2$ (3 h) followed by methanolysis. On treatment of 2 with two eq. dicyclohexylamine (DCHA), a 4:1 mixture of isomers E-3 and Z-3 is obtained. Recrystallization from methanol/ether ("Method 1 ") can give E-3 as a mono-dicyclohexylammonium ($DCHA^+$) salt (66%). Intriguingly, a different work-up [slow evaporation of solvent to crystallize 2 (E/Z ratio of 5:95), addition of 2 eq. DCHA and recrystallization from n-propanol/acetone; "Method 2"] gave pure Z-3, the first example of an isolated Z-hydroxyiminophosphonic acid, as a bis-$DCHA^+$ salt (62%). X-ray crystallographic analysis confirmed the structures of both the E-3 and Z-3 isomers.

In an additional aspect of the present invention, C-alkyl esters of 3 can be stable under physiological conditions but can be reactive under more vigorous conditions. The stability of the parent Troika acids in $H_2O$ were analyzed. Alkaline hydrolysis by methods known by those skilled in the art of E-3 and Z-3 (preferably, aq. NaOH, at a temperature of 25° C., at pH 13–14) can give the corresponding sodium salts E-4 and Z-4, the Z ester reacting much more rapidly (1 h vs. 70 h for E-3). Both salts 4 can be quite stable at high pH, typically, at pH values greater than 10, and room temperature, but at about pH 6 facile stereospecific fragmentations can be observed. E-4 ($t_{1/2}<10$ min) can produce exclusively orthophosphoric acid (5, $^{31}P$ NMR, δ 1.0 ppm), consistent with phosphorylation of the solvent, whereas Z-4 ($t_{1/2} \sim 15$ min) can give a product with an intact P-C bond, identified as cyanophosphonic acid 6. The transformation of anti α-keto acid oximes to nitriles in aqueous solution at 40–100° C. is well known to those skilled in the art, but the corresponding process giving a phosphononitrile from a phosphonate α-oxime, observed with Z-4, was unexpected. Furthermore, an additional unexpected result in accordance with the present invention, was the finding that simple removal of the carboxy alkyl group of E-3 can create a reagent (E-4) capable of phosphorylation under mild aqueous conditions.

With reference to FIG. 3, E-3 isomers, like Z-3 isomers, are stable at 22° C. (24 h by $^{31}P$ NMR) in $D_2O$ (pH 2–8). Heating of E-3 in a solvent selected from the group consisting of ethanol, isopropanol, t-butanol, water or acetonitrile (EtOH-i-PrOH, EtOH-t-BuOH, $H_2O$ or acetonitrile), gave products ($^{31}P$ NMR) suggesting monomeric metaphosphate-like fragmentation. E-3 fragmented over several hours in refluxing acetonitrile to yield (81%) products with $^{31}P$ NMR δ=–10 and –22, identified as polyphosphates, which are known to those skilled in the art as self-condensation products of metaphosphate. E-3 remained unchanged after 5 h in 1:1 MeOH: i-PrOH at 72° C., but after 30 h in 1:1 EtOH: i-PrOH at 79° C., forming Et phosphate and i-Pr phosphate (84%) in a ratio of 1.3:1. A similar experiment in 1:1 EtOH: t-BuOH gave a product ratio of ~2:1 Et phosphate: t-Bu phosphate. Lack of selectivity in phosphorylation of a primary alcohol vs. the sterically hindered t-butanol is a well known to those skilled in the art, as a criterion for a dissociative (metaphosphate) mechanism, and can exclude an associative-elimination phosphorylation mechanism, where a much larger EtOH: t-BuOH selectivity ratio would be expected. Heating E-3 in $H_2O$ (3.5 h, 82–84° C.) can give 100% conversion to phosphate at pH 4.0, and 88% conversion at pH ~6.5. The Z-isomer of 3 was stable for 4 h in 1:1 EtOH: i-PrOH at 79° C., and showed 46% conversion to a mixture of phosphate (28%), phosphononitrile 6 (13%; see below) and the E-isomer (5%) in $H_2O$ (5.7 h, 82–84° C.).

In accordance with the present invention, the position of the oxime hydroxy group in Troika acids can mediate phosphorylation vs. nitrile formation via alternative fragmentation pathways, with the carboxyl group controlling reactivity in neutral aqueous solution at ambient temperatures.

Figure 4:
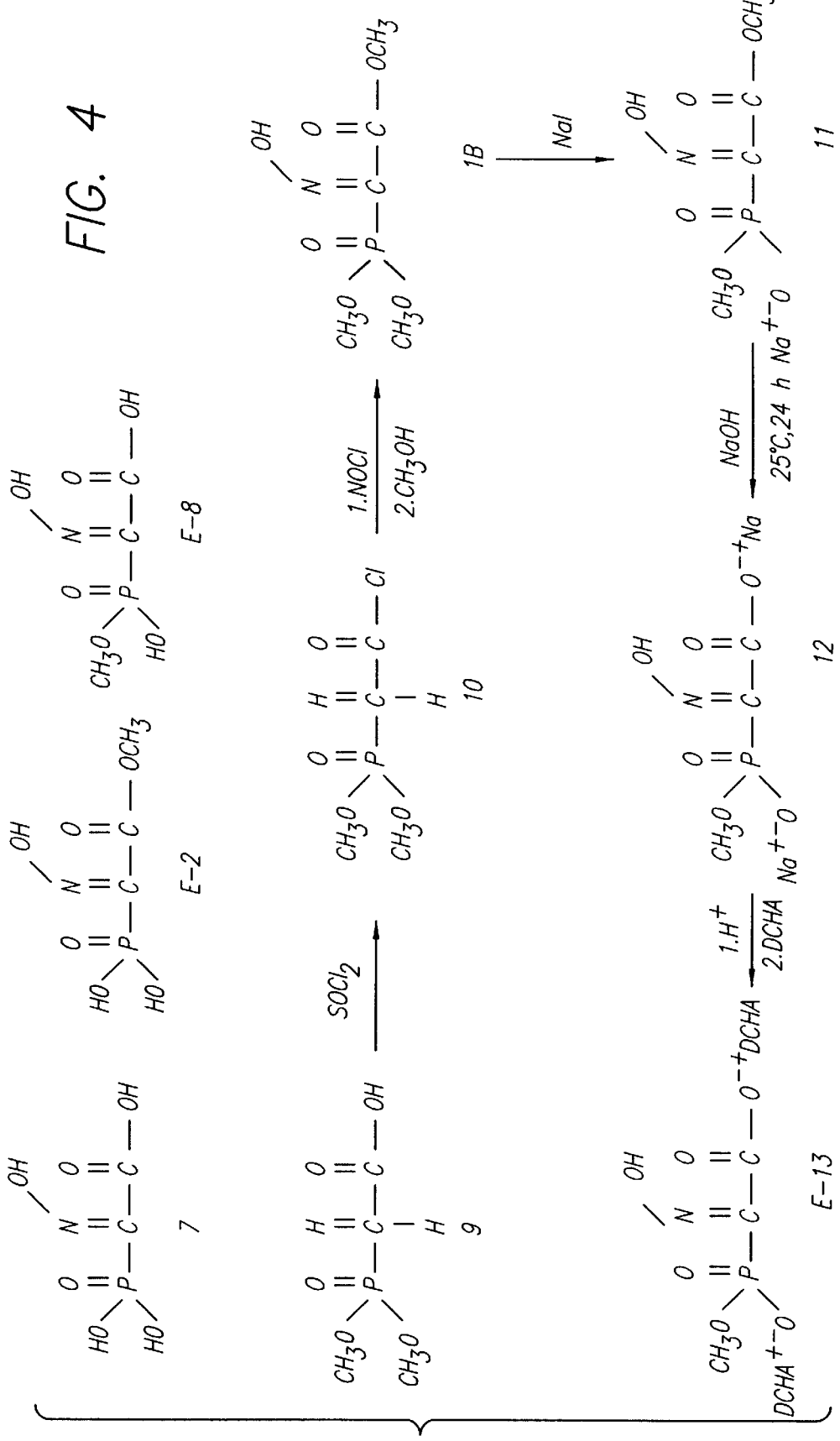
FIG. 4 shows synthesis of (E)-(hydroxyimino)-(hydroxymethoxyphosphinyl)acetic acid.

Synthesis of (E)-(Hydroxyimino) (hydroxymethoxyphosphinyl)acetic Acid and pH Fragmentation In contrast to both its parent "Troika' acid (E-7, a phosphorylating agent at pH 7 and 25° C.) and its C-methyl isomer (E-2, which is stable at both acidic and neutral pH), (E)-(hydroxyimino)(hydroxymethoxyphosphinyl)acetic acid E-8 was unreactive at pH 7 and 25° C. but at pH 1.5 fragmented to methyl phosphate (15%) and methyl phosphorocyanidate (85%) (see FIG. 4). The minor product is consistent with solvent phosphorylation, the reaction exclusively observed with E-7. In accordance with the present invention, a non-phosphorylating fragmentation pathway can be involved a preliminary E→Z isomerization of 8 prior to $C_\alpha$-$C_\beta$ cleavage. Dual fragmentation pathways can also be detected ($^{31}P$ NMR) when the $DCHA^+$ salt of E-8 (E-13) is heated in acetonitrile or EtOH; in addition to phosphorylation products (16–19%), methyl phosphorocyanidate 15 is formed (81–84%). Reaction of E-13 in refluxing EtOH: t-BuOH (1:1) shows low stereoselectivity in product formation (~3:1 ethyl methyl phosphate:t-butyl methyl phosphate), which is consistent with a dissociative phosphorylation process.

According to the present invention, the C-methyl ester of the E-Troika acid (E-2, as a monoanionic salt) was shown to give phosphorylation products when heated in acetonitrile (AN) or alcohols. Under neutral or moderately acidic conditions at room temperature E-2 (ionized in response to the pH) was stable in water at room temperature. Removal of the carboxy alkyl group of E-2 (e.g., by alkaline hydroysis) can create a phosphorylating agent (E-7) active under mild aqueous conditions (pH 7, 25° C.). Fragmentation of 7 can be stereospecific, the E isomer giving P-$C_\alpha$ bond cleavage, and the Z isomer undergoing $C_\alpha$-$C_\beta$ bond cleavage to form phosphorocyanidate.

Synthesis of the P-Monomethyl Isomer of E-2, E-8, and Fragmentation Behavior in Aqueous and Non-aqueous Solvents Synthesis of E-8 (FIG. 4). Trimethyl α-(hydroxyimino) phosphonoacetate 1B was obtained (48%) as a 7:3 E:Z mixture by nitrosation of the corresponding chlorocarbonyl compound 10 followed by methanolysis. Monodealkylation of 1B with NaI gave 11 (88:12 E:Z mixture), which was hydrolyzed by NaOH to the P-monoester disodium salt 12. The acid 8 was generated using an ion-exchange resin in $H^+$ form and trapped as an E/Z mixture of dicyclohexylammonium ($DCHA^+$) salts, from which the pure bis-$DCHA^+$ salt of E-8 (E-13) was obtained by recrystallization methods known to those skilled in the art.

Fragmentation of E-8. Like its C-methyl isomer E-2 [Kashemirov, B. A., et al., *J. Am. Chem. Soc.*, 117:7285–7286 (1995)], E-8 (from the salt E-13) was stable in water at about pH 7 for about 24 hours (room temperature).

However, in contrast to E-2, at pH 1.5, E-8 ($^{31}P$ NMR δ 2.4 ppm) quantitatively decomposed (FIG. 5) over 2.5 hours. The minor product, methyl phosphate 14 (15%; $^{31}P$ NMR δ 2.1 ppm) corresponded to a P-$C_\alpha$ bond cleavage, seen in E-1. The major product was methyl phosphorocyanidate 15 (85%; $^{31}P$ NMR δ 17.4 ppm) corresponding to $C_\alpha$-$C_\beta$ cleavage. As shown in FIG. 2, this pathway was only observed with the Z-isomer [Kashemirov, et al., supra] suggesting that E-8 undergoes acid-dependent isomerization to Z-8, which can then decarboxylate to 15. The predominantly trans elimination of α-hydroxyiminocarboxylic acids [Ahmad, A., et al., *Can. J Chem.*, 39:1340–1359 (1961)] is consistent with this idea. It is also supported by the observation of a small $^{31}P$ NMR peak at δ 0.2 ppm, assigned to Z-8, in reaction mixtures containing incompletely decomposed E-8. The product distribution observed in the system of FIG. 5 indicates that the overall process: E-8→Z-8→15 is about 6x faster than a dissociative fragmentation of E-8, whether to a putative methyl metaphosphate intermediate which should react rapidly with the solvent (FIG. 5), or via an analogous open transition state [Westheimer, F. H., *Chemical Reviews*, 81:313–326 (1981)].

E-2 (as a $DCHA^+$ salt) decomposed to polyphosphates after 1 d in refluxing AN, whereas methyl α-(hydroxyimino) benzylphosphonate anion (12, not shown) is thermally stable under similar conditions. E-8 (as the $DCHA^+$ salt E-13) resembles 12 in having a monoanionic phosphonate group that might be expected to be less reactive to fragmentation via a dissociative pathway than a potentially dianionic phosphonate such as E-7. E-13 in refluxing AN proved not to be stable, however, and the main P-$C_\alpha$ cleavage phosphorylation product (sym-dimethyl pyrophosphate, $^{31}P$ NMR; 16%) was dominated by an unexpected $C_\alpha$-$C_\beta$ cleavage product, methyl phosphorocyanidate (84%). Similar product partitioning was seen in refluxing EtOH (19% ethyl methyl phosphate, 81% methyl phosphorocyanidate). Replacement of the EtOH by 1:1 EtOH-t-BuOH resulted in a 1:3.3 ratio of ethyl: t-butyl methyl phosphate products (total 24%). Formation of polyphosphates in AN and phosphorylation at comparable rates of t-BuOH vs. primary alcohols are considered to be characteristic of dissociative phosphate and phosphonate fragmentations to those skilled in the art.

Thus, the possibility of trans elimination in both E and Z oxime isomers of Troika acids can be an important feature of these compounds. In the scheme of FIG. 5, both pathways can be accessed from one stereoisomer (E-8) because E→Z isomerization competes favorably with direct fragmentation.

The stability of E-2 at low pH and fragmentation-isomerization of E-8 under the same conditions indicates that these processes are facilitated in E-8 by intramolecular protonation of the oxime OH by the carboxyl proton. The stability of E-8, and the fragmentation of E-7 at pH 7 are consistent with a stereoelectronic control effect (E-7 vs. E-8 has the higher number of antiperiplanar lone pairs). Dissociative fragmentation of a methyl phosphonate monoanion such as E-8 at pH 7 would be more difficult than fragmentation of the dianion which can be available as an equilibrium species from 7 at this pH.

The stability of E-2 and E-8 under physiological aqueous conditions suggests that both types (P and C) of monoester could be precursors of E-7 via mild esterolytic hydrolysis, with an appropriate choice of the ester group.

Significance of p-Nitrophenyl (E)-(Hydroxyimino) (Dihydroxyphosphinyl) Acetate (PNHDA)

Figure 6:
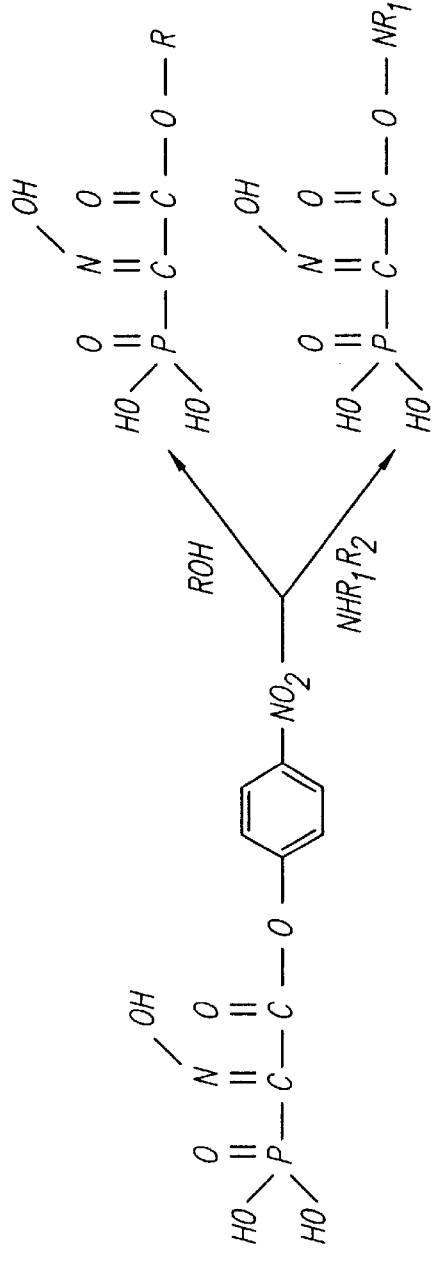
FIG. 6 shows the use of p-nitrophenyl (E)-(hydroxyimino)(dihydroxyphosphinyl) acetate (PNHDA) as a reagent for acyl-transfer reactions.

A method for preparing C-derivatives of "Troika Acid", namely by synthesis of an ester of the $CO_2H$ group of Troika acid, (COOR) or similar derivatives (COX), wherein the OR or X function is readily and conveniently replaced by a nucleophile function creating an ester, amide, or other carboxylic acid derivative, particularly one in which the said nucleophilic function comprises or is attached to a moiety that affords: 1) attachment to a polymeric support or resin; 2) selective recognition, and/or selective reactions, of specific molecules or biomolecules including enzymes; 3) a modification in the resulting product that can permit advantageous means of activation, by hydrolysis, reaction with other nucleophiles for the chemical cleavage, or other facile means, as a method of generating an active phosphorylating agent under mild conditions, or other specific conditions.

p-Nitrophenyl (E)-(hydroxyimino)(dihydroxyphosphinyl)acetate (PNHDA) is shown herein to be a convenient reagent for acyl-transfer reactions under mild conditions with different nucleophiles. This makes facile reactions possible with OH— and NH— containing nucleophiles, such as alcohols, hydroxy(amino)polymers, amines, amino acids, peptides and proteins, thereby creating novel compounds comprising one or more of the above structures with the "Troika" moiety, i.e., phosphoryl, hydroxyimino and carbonyl groups, still attached to the original carbon atom (see FIG. 6).

Reaction Between PNHDA and Alcohols or Amines

The compound (PNHDA), dissolved in polar solvents reacted with alcohols readily in the presence of triethyl amine as a catalyst or amines (usually without catalyst) at room temperature, giving the desired products in high yields. NMR $^{31}P$ and $^{13}C$ showed that the configuration of E isomer was not changed during these reactions.

SPECIFIC EXAMPLES

Model Nucleophilic Linking Reactions of PNHDA as a Route to Troika Acid Conjugates Amine Linking: Reaction of PNHDA with Butylamine. 100 mg of (PNHDA) was dissolved in 5 ml of fresh distilled (under KOH) butylamine. After 15 minutes, the solvent was removed using the water pump. The residue was acidified by Dowex $H^+$ in methanol. The resulting anilinium salt was recrystallized from methanol-ether, m.p. 114–115° C., yield 50% (characterized by $^1H$, $^{13}C$, $^{31}P$ NMR).

Alcohol Linking: Reaction of PNHDA with MethanoL 100 mg of (PNHDA) was dissolved in 5 ml of dry methanol, and 2 drops of triethyl amine were added at room temperature. After one hour, the solvent was removed under vacuum. The residue was acidified by Dowex $H^+$ in methanol. The product, DCHA salt, was recrystallized from methanol-ether, m.p. 143–144° C., yield 76% (characterized by $^1H$, $^{13}C$, $^{31}P$ NMR).

Photochemical Activation Example. 5 mg of o-Nitrobenzyl (E)-dihydroxyphosphinyl)(hydroxyimino) acetate (ONBCE-TA) (prepared analogously to PNHDA) dissolved in 0.5 ml of 100 mM Tris buffer (pH 6.9) was irradiated in a Rayonet apparatus for 17 hr at 39° C. Phosphoric acid (the product from phosphorylation of solvent water) was obtained, yield 11%. The phosphorylation was not noticed in the absence of UV irradiation.

Uses of α,α-Disubstituted Trifunctional Oxime Derivatives

Of equal or greater significance, the methods of the present invention make it possible to efficiently produce Troika acids and their derivatives in sufficient purity for a variety of uses known to those skilled in the art, some of which have been described above, which can include, pH sensitive chelating agents, enzyme activated drugs; drug delivery agents and phosphorylating reagents.

Figure 7:
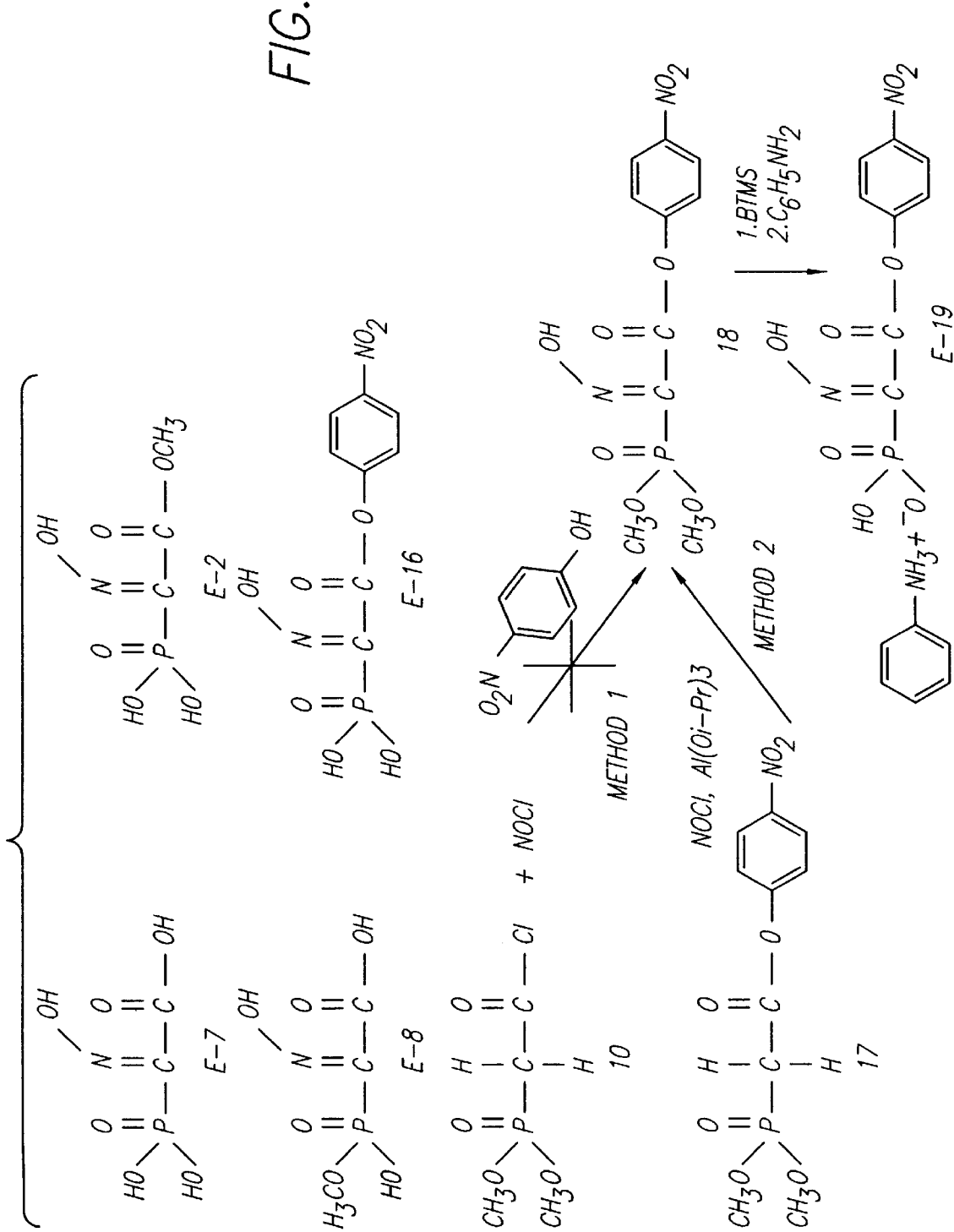
FIG. 7 shows the synthesis of PNHDA.

Synthesis of P-Nitrophenyl (E)-(Hydroxyimino) (Dihydroxyphosphinyl)acetate—a novel agent for phosphorylation under mild aqueous conditions.

p-Nitrophenyl carboxy esters, "Troika acid" ester precursors with a labile ester group, able to liberate active compounds under mild conditions, can be readily cleaved in the presence of water. In accordance with the present invention, the synthesis and phosphorylating properties of p-nitrophenyl (E)-(dihydroxyphosphinyl)(hydroxyimino) acetate E-16 are disclosed (see FIG. 7).

Synthetic Aspects. E-2 and E-8 can be obtained by nitrosation (NOCl) of the corresponding chlorocarbonyl compounds (FIG. 7, Method 1) followed by methanolysis and regioselective deakylation with $Me_3SiBr$ or NaI. However, this approach to synthesis of E-4 may not be useful, because of the low reactivity of phenols with chlorocarbonyl compounds. The dimethyl ester of E-4 can be synthesized by direct nitrosation of compound 17 (obtained by condensation of the corresponding acid with p-nitrophenol in the presence of DCC) with NOCl) ($CH_2Cl_2$) and $Al(Oi-Pr)_3$ at room temperature (Method 2). The reaction to form 18 can be monitored by TLC and $^{31}$NMR, and the reaction time is typically around 30 min. Compound 18 (mixture of E and Z isomers) can be obtained in 20% yield as slightly yellow crystals, composition and structure consistent with elemental analysis and NMR ($^1$H, $^{13}$C, $^{31}$P). Typically, regioselective didealkylation with $Me_3SiBr$ can be carried out in any polar solvent known to those skilled in the art. The regioselective didealkylation can be carried out at ambient temperature until the dealkylation is substantially complete, preferably for 3 hr. The solvent preferably is dry acetonitrile. Polar solvents can selectively. stabilize the E isomer (in acetonitrile E:Z ratio 3:1; in $CH_2Cl_2$, 1:1). Pure E-19 (anilinium salt) can be obtained by recrystallization from methanol-ether.

Figure 8:
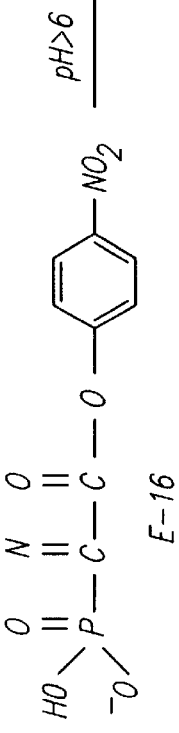
FIG. 8 shows hydrolysis and fragmentation of PNHDA.

Hydrolysis Chemistry. The anilinium salt E-19 is stable to storage, but in $H_2O$ can undergo hydrolysis-fragmentation, giving phosphate (FIG. 8). Decomposition of E-16 in $H_2O$ can be pH dependent: typically the pH is between about 2 to about 4. Preferably, when the pH is about 3, less than 4% (100% phosphate) decomposition occurred over 52 hr; at pH 6.5 $t_{1/2}$~30 hrs. (92% phosphate and 8% phosphorocyanidate). At pH 8.5 ($t_{1/2}$~1-hrs.) 80% phosphate and 20% phosphorocyanidate were obtained. At the same pH but in the presence of $Mg^{2+}$ hydrolysis takes place faster. Formation of phosphorocyanidate under these conditions was not observed, however an additional peak with δ –0.35 ppm in $^{31}$P NMR (assigned to E-7) was found. Formation of E-7 in hydrolysis of E-2 under alkaline conditions and E-16 under mild conditions suggests the same mechanism of phosphorylation for both cases: via E-7 as the precursor of active metaphosphate anion. Fragmentation of E-16 at pH 8.5 in 1:1 water:methanol gave a 1.2:1 mixture of phosphoric acid and methyl phosphate, correspondingly (total 34%).

Hydrolysis of both E-16 and p-nitrophenyl acetate is a pseudo-first order process. At pH 8.5 (25° C.) the rate of release of p-nitrophenoxide from E-16 is 20× faster than the rate of release of p-nitrophenoxide from p-nitrophenyl acetate. In the presence of 0.2 M $MgCl_2$, the hydrolysis rate for E-16 is enhanced by a factor of 2.5 (±0.1), whereas the hydrolysis rate for p-nitrophenyl acetate is not altered significantly. At 0.2 M $MgCl_2$, the rate of release of p-nitrophenoxide from E-16 is 40× faster than the rate of release of p-nitrophenoxide from p-nitrophenyl acetate. It is known to those skilled in the art that at pH 10 (27° C.) hydrolysis of p-nitrophenyl phosphonoacetate can be 250× slower than hydrolysis of p-nitrophenyl acetate. Qualitatively, the (E)-oxime group in E-16 appears to accelerate hydrolysis of itsp-nitrophenyl ester moiety by several orders of magnitude, making E-16 a $Mg^{2+}$ or $Ni^{2+}$ (see example below) sensitive phosphorylating agent under mild aqueous conditions.

The following Examples below illustrate one important embodiments of the method according to the present invention.

EXAMPLES

All reactions in these Examples were performed in scrupulously dried glassware under $N_2$. All solvents and reagents were of reagent grade quality, purchased commercially, and used without further purification, except as noted below. Acetone was dried with anhydrous $CaSO_4$ and then distilled. Dichloromethane was refluxed with and distilled from $CaH_2$. Neutral silica gel (30–60 mesh) was used for column chromatography.

NMR spectra were recorded on a Bruker AM 360 spectrometer. $^1$H and $^{13}$C NMR chemical shifts are referenced to external tetramethylsilane. $^{31}$P NMR chemical shifts are referenced to external 85% $H_3PO_4$. UV spectra were recorded on a Shimadzu UV-260 spectrometer. IR spectra were recorded on a Perkin-Elmer 281 spectrometer. Melting points were recorded on a Thomas Hoover apparatus.

Synthesis of P, P-Diethyl C-Methyl Ester of 1A. Oxime 1A was prepared by modification of a previously published method (Kashemirov, B. A.; Mikityuk A. D. Strepikheev, Y. A.; Khokhlov, P. S. *J Gen. Chem. USSR (Engl.)* 1986, 56, 843) herein incorporated by reference. The reaction time was limited to 5 h at room temperature. The crude product was conveniently purified by column chromatography on silica gel (30–60 mesh) (acetone/$CHCl_3$, 1:5). $^{13}$C NMR ($CDCl_3$): δ (ppm) 144.5 (E), (d, $^1J_{PC}$=221 Hz, P—C=N), 143.5 (Z), (d, $^1J_{PC}$=161 Hz, P—C=N). $^{31}$P NMR ($CDCl_3$): δ (ppm) 5.0 (E), 4.3 (Z). 4:1 E/Z.

Synthesis of E-3. Dicyclohexylammonium E-Methyl (Hydroxyimino)phosphonoacetate. A mixture of 1A (1.196 g, 0.005 mol) and BTMS (2.297 g. 0.015 mol) was refluxed in dry $CH_2Cl_2$ (20 ml) under $N_2$ for 3 h. Upon removal of the solvent in vacuo, the oily residue was treated with a solution of dicyclohexylamine (DCHA) (1.813 g, 0.01 mol) in MeOH (5 ml) at 0° C. for 10 min. The solvent was then evaporated in vacuo to leave the product, MP 143–144° C.; $^1$H NMR ($D_2O$): δ (ppm) 1.0–2.1 (m, 20 H, $CH_2$), 3.19 (m, 2H, CH), 3.84 (s, 3H, $OCH_3$); $^{13}$C NMR($D_2O$): δ (ppm) 24.1, 24.7, 29.2, 53.4 (cyclohexyl), 53.1 (s, $OCH_3$), 152.5 (d, $^1J_{PC}$=192 Hz, P—C=N), 165.1 (d, $^2J_{PC}$=20 Hz, C=O; $^{31}$P NMR ($D_2O$, pH=4.3): δ (ppm)-1.13. The structure was confirmed by X-ray crystallography.

Synthesis of Z-3. Bis(dicyclohexylammonium) Z-Methyl (Hydroxyimino)phosphonoacetate. A mixture of 1A (1.196 g, 0.005 mol) was refluxed with bromotrimethylsilane (BTMS) (2.297 g. 0.015 mol) in dry $CH_2Cl_2$ (20 ml) under $N_2$ for 3 h. Upon removal of the solvent in vacua, the oily residue was treated with MeOH (10 ml) at 10° C. for 10 min.

After repumping, the product slowly solidified over 24 h, MP 102–105° C. The crystalline solid was then dissolved in dry MeOH (5 ml) and treated with a solution of dicyclohexylamine (DCHA) (1.813 g, 0.01 mol) in MeOH (5 ml) at 0° C. for 10 min. The solvent was then evaporated in vacua and the resulting solid was recrystallized twice from n-propanol/acetone, yielding 1.685 g (62%) of Z-3, MP 171–172° C. $^1$H NMR (D$_2$O, pH=7.1): δ (ppm) 0.9–2.0 (m, 40H, CH$_2$), 3.06 (m, 4H, CH), 3.66 (s, 3H, OCH$_3$). $^{13}$C NMR (D2O, pH=7.1): δ (ppm) 23.8, 24.4, 28.9, 53.1 (cyclohexyl), 52.5 (s, OCH$_3$); 154.7 (d, $^1J_{PC}$=131 Hz, P—C≡N), 165.9 (d, $^2J_{PC}$=19 Hz, C=O). $^{31}$P NMR (D$_2$O, pH=7.1): δ (ppm) 2.38. The structure was confirmed by X-ray crystallography. Extended drying of E-3 and Z-3 tended to remove some DCHA.

Synthesis of E4 & 5. 10 N NaOH (0.5 ml) was added to E-3 (10 mg) in D$_2$O (0.4 ml) in an NMR tube, raising the pH to ~13. Hydrolysis was monitored by $^1$H and $^{31}$P NMR at room temperature. The reaction was complete in 3 d, giving a product identified by $^{13}$C and $^{31}$P NMR as E-4. $^{13}$C NMR (D$_2$O): δ (ppm) 161.8 (d, $^1J_{PC}$=176 Hz, P—C≡N), 175.4 (d, $^2J_{PC}$=21 Hz, C=O); $^{31}$P NMR (D$_2$O, pH=13–14): δ (ppm) 2.8.

Acidification of E-4. Acidification of E-4 to pH 5.7 [$^{31}$P NMR, D$_2$O, δ (ppm) 1.06] resulted in its rapid (t$_{1/2}$<10 min) decomposition to inorganic phosphate 5, identified by $^{31}$P NMR [D$_2$O, δ (ppm) 1.00].

Acidification of Z-4 & 6. An analogous procedure for E-4 was carried out with the Z-3 isomer. Hydrolysis was complete within 1 h, yielding Z-4. $^{31}$C NMR (D$_2$O, pH=13–14): δ (ppm) 161.1 (d, $^1J_{PC}$=127 Hz, P—C≡N), 171.9 (d, $^1J_{PC}$=127 Hz, P—C≡N), 171.9 (d, $^2J_{PC}$=17 Hz, C=O); $^{31}$P NMR (D$_2$O, pH=13–14): δ (ppm), 2.0. When the pH of the Z-4 [$^{31}$P NMR, D$_2$O, δ (ppm) 10] solution was lowered to 6, rapid (t$_{1/2}$~5 min) decomposition of Z-4 to cyanophosphonate 6 (see below) was observed: $^{31}$P NMR (D$_2$O, pH=6): δ (ppm)-14.6; $^{31}$C NMR (D$^2$O): δ (ppm, pH =6) 123.5, (d, $^1J_{P-C}$=145 Hz, P—C≡N). These data are consistent with those of the authentic compound prepared from dimethyl cyanophosphonate as described below.
The following compounds were prepared independently to verify the structure of 6:

Synthesis of Dimethyl Cyanophosphonate. This compound was prepared from trimethylphosphite and cyanogen bromide according to the literature method (Shiori, T.; Yokoyama, Y., Kasai, Y. and Yamada, S. Tetrahedron, 1976, 32, 2211) herein incorporated by reference: bp 50–51° C./1 mM Hg (lit. 65–66° C./4 mM Hg). $^1$H NMR (CDCl$_3$): δ (ppm) 3.80 (d, 6H, $^3J_{H-P}$=13 Hz, 2CH$_3$) [lit. δ (ppm), 3.90 (d, 6H, $^3J_{H-P}$=13 Hz, 2CH$_3$)]. $^{31}$P NMR {$^1$H } (CDCl$_3$): δ (ppm)-17.60 (s). $^{31}$P NMR (CDCl$_3$): δ (ppm)-17.60 (septet, $^3J_{PH}$=13 Hz). $^{13}$C NMR (D20): 6 (ppm) 55.70 (d, $^2J_{CP}$=7 Hz), 113.42 (d, $^1J_{CP}$=214 Hz) IR (neat): 2201 cm$^{-1}$ (lit. 2200 cm$^{-1}$).

Synthesis of Methyl Cyanophosphonate. NaI (0.33 g, 2.2 mol.) was added to a solution of dimethyl cyanophosphonate (0.30 g, 2.2 mole) in dry acetone (2 ml) at room temperature. After 10 min, the resulting white precipitate was filtered at the pump and washed with dry acetone, yielding 0.25 g (80%) of white powder. For NMR spectra, 50 mg of the product was dissolved in D$_2$O in a 5 mM NMR tube and the pH was adjusted with 3 N HCl to 1.5. $^1$H NMR (D$_2$O): δ (ppm) 3.60 (d, 3H, $^3J_{HP}$=13 Hz, CH$_3$). $^{31}$P NMR {$^1$H} (D$_2$O): δ (ppm)-17.44 (q, $^3J_{PH}$=13 Hz). $^{13}$C NMR (D$_2$O): δ (ppm) 53.60 (d, $^2J_{CP}$=6 Hz), 117.41 (d, $^1J_{CP}$=181 Hz).

Synthesis of Cyanophosphonic Acid. BTMS (0.85 g, 5.55 mole) was added to dimethyl cyanophosphonate (0.25g, 1.85 mole). The reaction mixture was maintained at room temperature under anhydrous conditions for 4 d. Excess BTMS was then removed in vacua and 2 ml MeOH was added to the residue. The solvent was reevaporated and the residue was dissolved in 1 ml D$_2$O. The pH of NMR samples was adjusted to 5 with NaHCO$_3$. $^{31}$P NMR {$^1$H} (D$_2$O): δ (ppm)-14.75(s) (main peak). $^{13}$C NMR (D$_2$O): δ (ppm) 123.10 (d, $^1J_{CP}$=146 Hz).

Synthesis of DCHA$^+$ Salt of Cyanophosphonic Acid. Cyanophosphonic acid was prepared as described above, then 3 eq. of dicyclohexylamine (DCHA) in MeOH was added to the MeOH solution of cyanophosphonic acid. Addition of Et$_2$O precipitated the DCHA$^+$ salt. This was filtered and recrystallized from MeOH/Et$_2$O. $^1$H NMR (D$_2$O): δ (ppm) 1.0–2.0 (m, 10H, 5CH$_2$), 3.09 (m, 1H CH). $^{31}$P NMR {$^1$H} (D$_2$O): δ (ppm)-15.10 (s). $^{13}$C NMR (D$_2$O): δ (ppm) 24.43, 25.19, 29.59, 53.46 (cyclohexyl ring), 124.57 (d, $^1J_{CP}$=144 Hz).

pH Dependence of the Stability of DCHA$^+$ Salts 3. These experiments were carried out in 5 mm glass NMR tubes in D$_2$O at 22° C., concentration of 3 0.1% (w/v). The results are shown in Tables 1 and 2.

TABLE 1 pH Dependence of the Stability of Z-3 = Bis(dicyclohexylammonium) Z-methyl (hydroxyimino)phosphonoacetate

| | | | $^{31}$P NMR: δ ppm (%, int)[a] | | | |
|---|---|---|---|---|---|---|
| | | | | t = 24 h | | |
| Exp | pH | t = 0 | Z[b] | E[c] | H[d] | F[e] |
| 1 | 2.0 | −3.96 (100) | −3.96 (100) | | | |
| 2 | 4.2 | −2.79 (100) | −2.79 (100) | | | |
| 3 | 6.7 | 2.24 (100) | 2.24 (95.0) | −0.78 (5.0) | | |
| 4 | 8.3 | 2.45 (100) | 2.45 (92.6) | −0.70 (7.4) | | |
| 5 | 10.4 | 2.43 (100) | 2.43 (87.2) | −0.70 (8.5) | 1.80 (2.6) | −14.7 (1.7) |
| 6 | 11.0 | 2.44 (100) | 2.44 (76.3) | | 1.93 (14.5) | −14.7 (9.2) |

[a]% Amounts were obtained by integration of $^{31}$P NMR signals during the reactions.
[b]Z-isomer.
[c]E-isomer.
[d]Hydrolysis product 4.
[e]Fragmentation product (HO)$_2$P(O)CN.

TABLE 2 pH Dependence of the Stability of E-3 = Dicyclohexylammonium E-methyl (hydroxyimino)phosphonoacetate

| | | | $^{31}$P NMR: δ ppm (%, int)[a] | | | |
|---|---|---|---|---|---|---|
| | | | | t = 24 h | | |
| Exp | pH | t = 0 | E[c] | Z[b] | H[d] | F[e] |
| 1 | 2.0 | −1.06 (100) | −1.06 (100) | | | |
| 2 | 4.0 | −1.08 (100) | −1.08 (100) | | | |
| 3 | 6.2 | −0.78 (100) | −0.78 (91.1) | 2.20 (8.9) | | |
| 4 | 8.1 | −0.66 (100) | −0.66 (91.3) | 2.47 (8.7) | | |
| 5 | 10.4 | −0.48 (100) | −0.48 (87.2) | 2.46 (3.0) | 0.61 (6.9) | 3.69 (1.2) |
| 6 | 11.0 | −0.10 (100) | −0.10 (76.2) | 2.44 (1.8) | 0.61 (18.4) | 3.53 (3.6) |

[a]% Amounts were obtained by integration of $^{31}$P NMR signals during the reactions.
[b]Z-isomer.
[c]E-isomer.
[d]Hydrolysis product 4.
[e]Fragmentation product $(HO)_2P(O)OH$.

Stability of DCHA$^+$ Salts 3 Heated in Different Solvents. 40 mg 3 (E or Z) was heated in 5 ml of alcohol mixture, $H_2O$ or acetonitrile. Reaction progress was monitored by $^{31}$P NMR spectroscopy. The results are shown in Table 3.

TABLE 3

Stability of DCHA$^+$ Salts 3 in Alcohols, $H_2O$ or Acetonitrile at 72–84° C.

| Exp | isomer | solvent | t, °C. | time, h | products (yield, %) |
|---|---|---|---|---|---|
| 1 | E | MeOH:i-PrOH 1:1 | 72 | 5.5 | s.m.[a] recovered (100) |
| 2 | E | EtOH:i-PrOH 1:1 | 79 | 30 | Et-phosphate (48.3), i-Pr-phosphate (35.8), phosphate (8.5), Z-isomer (2.5), s.m. (4.9) |
| 3 | E | EtOH:t-BuOH 1:1 | 79 | 28 | Et-phosphate (33.9), t-Bu-phosphate (16.9), phosphate (9.4), Z-isomer (29.4), s.m. (10.4) |
| 4 | E | $H_2O$ (pH 4.0) | 82–84 | 3.5 | phosphate (100) |
| 5 | E | $H_2O$ (pH 6–7) | 82–84 | 4.0 | phosphate (87.7), s.m. (12.3) |
| 6 | E | MeCN | 81 | 3.5 | polyphosphates (80.9), s.m. (16.4), phosphate (0.6), phosphononitrile (2.1) |
| 7 | Z | EtOH:i-PrOH 1:1 | 79 | 4.0 | s.m. (100) |
| 8 | Z | $H_2O$ (pH 6–7) | 82–84 | 5.7 | s.m. (54.1), phosphate (27.8), phosphononitrile (13.4), E-isomer (4.7) |

[a]s.m. = starting material

Test for Cyanide. A drop of the 0.1 M test solution at pH 7 was mixed in a micro test tube with several drops of 1–2 mg p-benzoquinone in 1 ml of dimethyl sulfoxide. A dark brown color with green fluorescence indicated the presence of cyanide. The test was done for E-3, NaCN and E-4 (after fragmentation). A sample of E-4 after fragmentation gave a positive test for CN$^-$ that nicely matched (visually) the control sample of NaCN.

Trimethyl α-Hydroxyimino)phosphonoacetate 1B. Oxime 1B was prepared as previously described, but the reaction conditions were 5 h at room temperature and 9, obtained here by acidification of the corresponding potassium salt using Dowex 50WX8 (H$^+$ form), was used as the starting material. The product was purified by column chromatography on silica gel (30–60 mesh) (CHCl$_3$/acetone, 5:1), yield 48%. $^1$H NMR (CDCl$_3$):δ (ppm) 3.7–3.9 (m, 9H, OCH$_3$), 12.4 (s. 1H, OH). $^{13}$C NMR (CDCl$_3$): δ (ppm) 143.5 (E), (d, $^1J_{CP}$=224 Hz, P—C=N), 143.1 (Z), (d, $^1J_{CP}$=164 Hz, P—C=N). $^{31}$P NMR (CDCl$_3$): δ (ppm) 7.7 (E), 6.2 (Z). Calcd for C$_5$H$_{10}$NO$_6$P: C, 28.45; H, 4.77; N, 6.63. Found: C. 28.09; H, 4.79; N, 6.48.

Sodium Salt (11) of Methyl (Hydroxyimino)-(hydroxymethoxyphosphinyl)acetate. A solution of 1B (420 mg. 1.99 mole) in dry acetone (5 ml) was added to a solution of NaI (328 mg. 2.19 mole) in dry acetone (5 ml) at room temperature. After 24 h the precipitate was filtered and washed with dry acetone and Et$_2$O, yielding 320 mg (73.4%) 11 as a white solid. dec. 143° C. $^1$H NMR (D$_2$O): δ (ppm) 3.42 (E), (d, $^3J_{HP}$=11.5 Hz, OCH$_3$), 3.39 (Z), (d, $^3J_{HP}$=11.5 Hz OCH$_3$). 3.71 (E), (s, OCH$_3$), 3.68 (Z), (s, OCH$_3$). $^{13}$C NMR (D$_2$O): δ (ppm) 52.4 (d, $^2J_{CP}$=5.4 Hz, OCH$_3$), 52.7 (s, OCH$_3$), 150.0 (d, $^1J_{CP}$=193 Hz, P—C=N), 164.4 (d, $^2J_{CP}$= 20 Hz, C=O). $^{31}$P NMR (D$_2$O): δ (ppm) 2.14 (E), -0.75 (Z).

Bis-DCHA$^+$ Salt (E-13) of (E)-(Hydroxyimino)-(hydroxymethoxyphosphinyl)acetic Acid E-8. A solution of NaOH (100 mg. 2.5 mole) in H$_2$O (25 ml).was added to a solution of 11 (273 mg. 1.25 mole) in H$_2$O (2 ml) at 5° C. After 24 h without cooling, the solvent was removed in vacuo. The residue was dissolved in 0.5 ml H$_2$O and 1 ml MeOH and the acid E-8 was generated by filtration through Dowex 50WX8 (H$^+$ form). The filtrate was immediately treated with DCHA (3 eq.) in MeOH (5 ml). The mixture was evaporated in vacua and the residue recrystallized from n-propanol/acetone, giving 350 mg (51.3%) of E-13 as white crystals: MP 141–142° C. $^1$H NMR (D$_2$O): δ (ppm) 1.0–2.1 (m, 40H, CH$_2$), 3.19 (m, 4H, CH), 3.54 (d, 3H, OCH$_3$, $^3J_{HP}$=11 Hz). $^{13}$C NMR (D$_2$O): δ (ppm) 23.8, 24.4, 28.9, 53.0 (cyclohexyl), 52.4 (d, $^2J_{CP}$=5.4 Hz), 156.4 (d, $^1J_{CP}$=185 Hz, P—C=N), 168.8 (d, $^2J_{CP}$=18 Hz, C=O). $^{31}$P NMR (D$_2$O): δ (ppm) 4.2. Calcd for C$_{27}$H$_{52}$N$_3$O$_6$P: C, 59.43; H, 9.60; N, 7.70. Found: C, 59.17; H, 9.74; N, 7.65. Generation of the acid form, as described above but in MeOH provided it (major product) as a 1:1 mixture of E:Z isomers. $^{31}$P NMR (D$_2$O): δ (ppm) 2.4 (E), -0.2 (Z). $^{13}$C NMR (CDCl$_3$, C$_2$D$_6$O): δ (ppm) 146.8 (d, $^1J_{CP}$=212 Hz, P—C=N) (E), 144.4 (d, $^1J_{CP}$=157 Hz, P—C=N) (Z).

pH Dependence of the Stability of E-8. These experiments were carried out in 5 mm glass NMR tubes at 25° C., concentration of E-8 [prepared from E-13 by treatment with Dowex 50X8 (H$^+$ form)] 0.1% in D$_2$O (w/v).

Stability of E-3 When Heated in Different Solvents. A solution of 40 mg E-13 in 5 ml of solvent (AN, EtOH or EtOH-t-BuOH) was heated to reflux and reaction was monitored by $^{31}$P NMR.

p-Nitrophenyl (Hydroxyimino)(dimethoxyphosphinyl) acetate 18. $^1$H NMR (CDCl$_3$): (ppm) 3.93 (dd, 6H, OCH$_3$), 7.37, 8.24 (dd, 4H, C$_6$H$_4$). $^{13}$CNMR (CDCl$_3$, C$_3$D$_6$O): δ (ppm) 143.5 (E), (d, $^1$J$_{CP}$=220Hz, P—C=N), 143.3 (Z), (d, $^1$J$_{CP}$=166 Hz, P—C=N). $^{31}$P NMR (CDCl$_3$): δ (ppm) 6.6 (E), 6.3 (Z). Calcd for C$_{10}$H$_{11}$N$_2$O$_8$P: C 37.75; H, 3.48; N, 8.80. Found: C, 37.87; H, 3.55; N, 8.66.

Anilinium Salt of p-Nitrophenyl (E)-(Hydroxyimino)(dihydroxyphophinyl)acetate E-4. $^1$H NMR (D$_2$O): δ (ppm) 7.2–7.3 (m, 5H, C$_6$H$_5$), 7.42, 8.23 (dd, 4H, C$_6$H$_4$). $^{13}$C NMR (D$_2$O, C$_3$D$_6$O): δ (ppm) 151.2 (E), (d, $^1$J$_{CP}$=195 Hz, P—C=N). $^{31}$P NMR (D$_2$O, C$_3$D$_6$O): δ (ppm)-2.3. Calcd for C$_{14}$H$_{14}$N$_3$O$_8$P(H$_2$O)0.5: C 42.87; H, 3.85; N, 10.71. Found: C, 43.01; H, 3.77; N, 10.74.

Stability of E-19. These experiments were carried out in 5 mm glass NMR tubes at 22° C., concentration of E-4 0.1% (w/v).

Kinetic Measurements of the Hydrolysis of E-19. Reaction conditions: 25° C., µ=1.0 M (maintained with NaCl), pH 8.5 (0.01M Borate buffer), [E-19]~50–70 µM, [p-nitrophenyl acetate]=50 µM, [Mg$^{2+}$]=0–0.2 M. Rates were determined by spectrophotometric measurement of p-nitrophenoxide (λ 400 nm, Shimadzu UV-260 spectrophotometer; the temperature was controlled (±0.1° C.) with a VWR model 1165 circulating constant-temperature bath. The cell compartment temperature was measured with a standard thermometer. The alkaline hydrolysis of E-19 and p-nitrophenyl acetate showed pseudo-first order kinetics and the observed pseudo-first order rate constants were determined by a least-squares fit using Microsoft Excel on a Macintosh Performa 636.

Kinetic methods

The rates of hydrolysis of p-nitrophenyl(hydroxyimino)-(dihydroxyphosphinyl)acetate (16) were determined with Shimadzu UV-260 spectrophotometer by monitoring appearance of thep-nitrophenol at 400 nm (pH 6–11) and 317 nm (pH 4–5) and disappearance of reactant (16) at 217 nm (pH 4–5). The product spectra were quantitatively identified with those of equivalent concentration of p-nitrophenol under the same conditions. Reaction mixture pH values were measured. at 25 and 50° C. with a Beckman Model 71 pH meter. For non-metal ion-assisted reactions, a few buffer solutions were prepared with EDTA (2×10$^{-5}$) as a precaution against trace metal ions in the buffer and salts, but the same results were obtained as with the non-EDTA-containing buffers. Buffers employed were acetate (pH 4.2–5.3), N-ethyl morpholine (pH 6.7–7.8), and borate (pH 8–11). The buffer concentrations were 0.02–0.01 M (no significant catalytic effect). The ionic strength was 0.5–1.0 M, maintained with NaCl.

To initiate a kinetic run, 50–100 µl of 19 stock solution (0.002 M in H$_2$O) was injected into 2–3 ml of reactant solution maintained at the desired temperature. The reactions followed pseudo-first-order kinetics for at least 3 half-lives. Kinetic parameters were calculated with a linear least-squares computer program.

TABLE 4 pH dependence (w & w/o metal)

| | absence ion metal (T = 25° C.) | | | | absence ion metal (T = 50° C.) | | | | Ni = 0.01M (T = 50° C.) | | | |
|---|---|---|---|---|---|---|---|---|---|---|---|---|
| PH | K | K' | log (k) | log (K') | K | K' | log (k) | log (K') | K | K' | log (k) | log (K') |
| 8.5 | 0.052 | 0.05635 | −1.288 | −1.249 | | | | | | | | |
| 9 | 0.101 | 0.101 | −0.997 | −0.996 | | | | | | | | |
| 9.5 | 0.33 | 0.33 | −0.481 | −0.481 | | | | | | | | |
| 10 | 0.629 | 0.603 | −0.201 | −0.22 | | | | | | | | |
| 11 | 1.2 | 1.249 | 0.079 | 0.0966 | | | | | | | | |
| 7.4 | | | | | 0.0563 | 0.0605 | −1.249 | −1.22 | | | | |
| 6.5 | | | | | 0.011 | 0.009 | −1.959 | −2.05 | | | | |
| 5.2 | | | | | 0.0156 | 0.0165 | −1.807 | −1.78 | | | | |
| 4.2 | | | | | 0.0049 | | −2.311 | | | | | |
| 7.4 | | | | | | | | | 1.127 | 1.1 | 0.052 | 0.041 |
| 6.5 | | | | | | | | | 0.31 | | −0.509 | |
| 4.2 | | | | | | | | | 0.015 | | −1.824 | |

Figure 9:
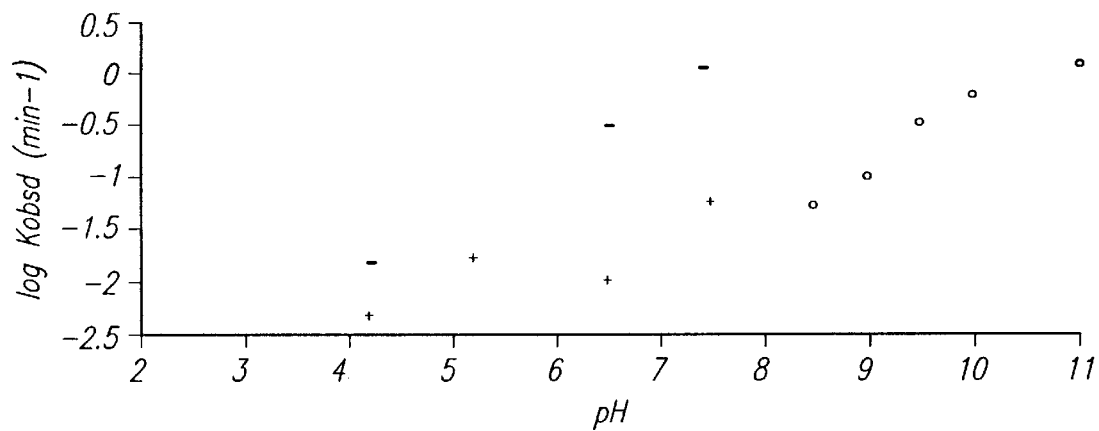
FIG. 9 shows kinetic measurements of log $K_{obsd}$ vs pH for the hydrolysis of PNHDA.
Figure 10:
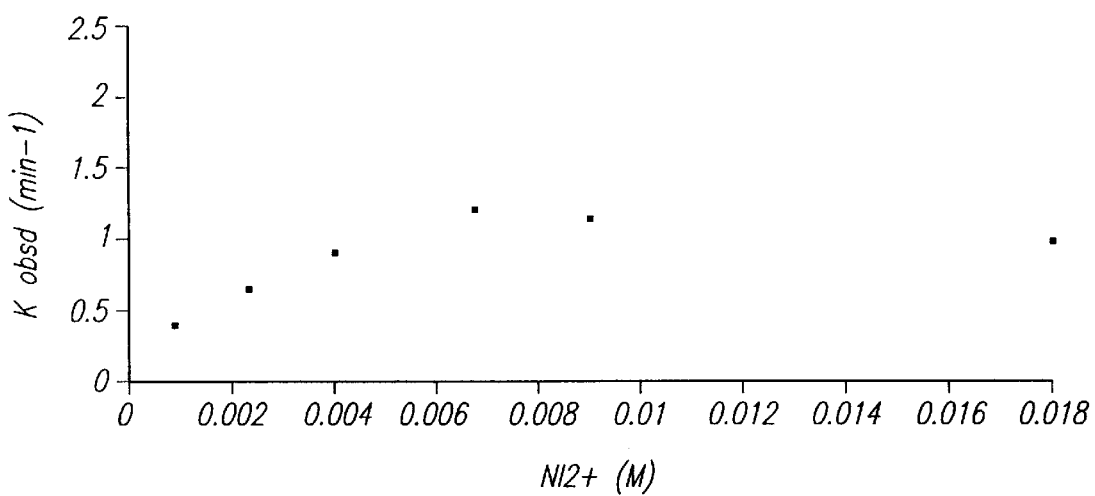
FIG. 10 shows kinetic measurements of $K_{obsd}$ vs $Ni^{2+}$ concentration for hydrolysis of PNHDA.

In FIG. 9 is shown a plot of log K$_{obsd}$ vs pH for the hydrolysis of PNHDA(1) in H$_2$O at 25° C. and 50° C. and u=0.5–1.0 M (see Table 4). The reactions at pH>8 are hydroxide ion catalyzed; the slope of the plots of log K$_{obsd}$ vs pH is 0.8. The reactions at pH<7 are independent of hydroxide ion concentrations. Hydrolysis of the ester is markedly enhanced by 0.01 M Ni$^{2+}$ ion (a saturating concentration). As seen in FIG. 9, only OH$^-$ catalysis is observed in the presence of Ni$^{2+}$ even at pH values as low as 4.2. The values of K$_{obsd}$ with 0.01M Ni$^{2+}$ at pH 6.5 and 7.4 are enhanced by a factor of 28 and 20 respectively, whereas at pH 4.2 the rate is enhanced only by a factor of 3. FIG. 10 illustrates the dependence on Ni$^{2+}$ concentration. The plot of K$_{obsd}$ vs Ni$^{2+}$ conc. is hyperbolic at constant pH with saturation effect as low as 0.007 M.

The previously described present invention has many advantages. The advantages include the discovery of novel α-(hydroxyimino) phosphonoacetic acids and derivatives, and methods for synthesizing them in a simple, fast, efficient manner with high yields, The versatility and the applications of these derivatives, makes these compounds especially valuable.

Although the present invention has been described in considerable detail with reference to certain preferred versions, other versions are possible. Thus, the spirit and scope of the appended claims should not be limited to the description of the preferred versions contained herein.

What is claimed is:

1. A compound comprising the general formula:

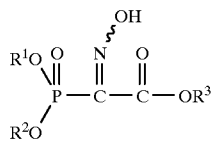

wherein N~OH denotes a bond between a nitrogen and oxygen of the OH which represents the Z or E isomeric form; $R^1$, $R^2$, and $R^3$ is selected from the group consisting of hydrogen, alkyl, and aryl; at least two of $R^1$, $R^2$, and $R^3$ are hydrogen; and either $R^1$ or $R^3$ is alkyl or aryl.

2. The compound of claim 1, wherein said alkyl or aryl group is selected from the group consisting of methyl, ethyl, propyl, butyl, benzyl, and phenyl.

3. An E-isomer of the compound of claim 1.

4. A Z-isomer of the compound of claim 1.

5. A salt of the compound of claim 1 comprising the general formula,

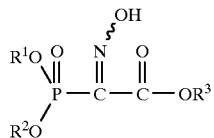

wherein $R^1$, $R^2$, and $R^3$ are selected from the group consisting of hydrogen, alkyl, aryl, sodium, and alkyl or aryl ammonium; at least two of $R^1$, $R^2$, and $R^3$ are each selected from the group, consisting of hydrogen, sodium, and alkyl or aryl ammonium; and either $R^1$ or $R^3$ is alkyl or aryl.

6. The salt of claim 5, wherein the alkyl ammonium at $R^1$ is dicyclohexylammonium and $R^3$ is methyl, ethyl, propyl, butyl, benzyl, or phenyl.

7. The salt of claim 5, wherein $R^1$ is alkyl or aryl and $R^2$ and $R^3$ are both alkyl or aryl ammonium.

8. The salt of claim 7, wherein $R^1$ is methyl, ethyl, propyl, butyl, benzyl, or phenyl and the alkyl ammonium at both $R^2$ and $R^3$ is dicyclohexylammonium.

9. A compound comprising the general formula,

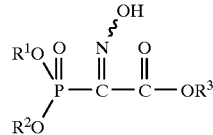

wherein N~OH denotes a bond between a nitrogen and oxygen of the OH which represents the Z or E isomeric form; $R^1$ and $R^2$ are selected from the group consisting of hydrogen, alkyl, aryl, and alkyl or aryl ammonium; and $R^3$ is a substituted aromatic compound.

10. The compound of claim 9, wherein the substituted aromatic compound at $R^3$ is p-nitrophenyl or o-nitrobenzyl.

11. The compound of claim 9, wherein $R^1$ and $R^2$ are methyl, ethyl, propyl, butyl, benzyl, or phenyl.

12. The compound of claim 9, wherein $R^1$ is hydrogen and $R^2$ is alkyl or aryl ammonium.

13. The compound of claim 12, wherein the aryl ammonium at $R^2$ is anilinium and the substituted aromatic compound at $R^3$ is p-nitrophenyl.

* * * * *